US009510916B2

(12) United States Patent
Voillat

(10) Patent No.: US 9,510,916 B2
(45) Date of Patent: Dec. 6, 2016

(54) SURGICAL SYSTEM, IN PARTICULAR DENTAL SURGICAL SYSTEM

(71) Applicant: Dassym SA, Hauterive (CH)

(72) Inventor: Jean-Pierre Voillat, Montavon (CH)

(73) Assignee: DASSYM SA, Hauterive (CH)

( * ) Notice: Subject to any disclaimer, the term of this patent is extended or adjusted under 35 U.S.C. 154(b) by 46 days.

(21) Appl. No.: 14/406,887

(22) PCT Filed: Jun. 6, 2013

(86) PCT No.: PCT/EP2013/061740
§ 371 (c)(1),
(2) Date: Dec. 10, 2014

(87) PCT Pub. No.: WO2013/186123
PCT Pub. Date: Dec. 19, 2013

(65) Prior Publication Data
US 2015/0125815 A1    May 7, 2015

(30) Foreign Application Priority Data

Jun. 11, 2012 (CH) .................................... 814/12

(51) Int. Cl.
*A61C 1/06* (2006.01)
*A61C 1/00* (2006.01)
(Continued)

(52) U.S. Cl.
CPC ......... *A61C 1/0015* (2013.01); *A61B 17/1626* (2013.01); *A61C 1/003* (2013.01); *A61C 1/06* (2013.01); *A61C 1/088* (2013.01)

(58) Field of Classification Search
CPC ........ A61C 1/003; A61C 1/06; A61C 1/088; A61C 1/0015; A61B 17/1626
See application file for complete search history.

(56) References Cited

U.S. PATENT DOCUMENTS 5,235,261 A * 8/1993 Philipp .............. A61B 17/1626
318/504
5,538,423 A * 7/1996 Coss .................... A61C 1/0015
408/8
(Continued)

FOREIGN PATENT DOCUMENTS

EP    0688539 A1    12/1995
EP    1753360 B1    2/2007
(Continued)

OTHER PUBLICATIONS

International Search Report for PCT/EP2013/061740 dated Jul. 24, 2013.
(Continued)

*Primary Examiner* — Ralph Lewis
(74) *Attorney, Agent, or Firm* — Pearne & Gordon LLP

(57) ABSTRACT

Surgical system, in particular a dental system including a surgical instrument, in particular a dental instrument and a device for controlling the electronic instrument. The device for controlling the electronic instrument includes a first electronic module. The instrument includes a rotary motor for driving the tool and a second electronic module. The rotary motor of the instrument is electrically powered by the first electronic module of the control device through the first electrical conductors dedicated to supply the rotary motor. The instrument is powered and/or electrically controlled by the first electronic module of the control device only through the second electrical conductors distinct from the first electrical conductors. The system also includes a management module of the second electrical conductors for sending on the second electrical conductors a number of signals larger to a number of second electrical conductors.

15 Claims, 13 Drawing Sheets

(51) Int. Cl.
*A61B 17/16* (2006.01)
*A61C 1/08* (2006.01)

(56) References Cited

U.S. PATENT DOCUMENTS

| | | | |
|---|---|---|---|
| 6,102,695 A * | 8/2000 | Rosenstatter | A61B 1/00179 433/29 |
| 8,398,394 B2 * | 3/2013 | Sauter | A61B 17/1626 433/27 |
| 2006/0240382 A1 | 10/2006 | Voillat | |
| 2011/0266124 A1 | 11/2011 | Culp et al. | |

FOREIGN PATENT DOCUMENTS

| WO | 2005037124 A1 | 4/2005 |
|---|---|---|
| WO | 2005115264 A1 | 12/2005 |

OTHER PUBLICATIONS

Written Opinion for PCT/EP2013/061740 dated Jul. 24, 2013.

* cited by examiner

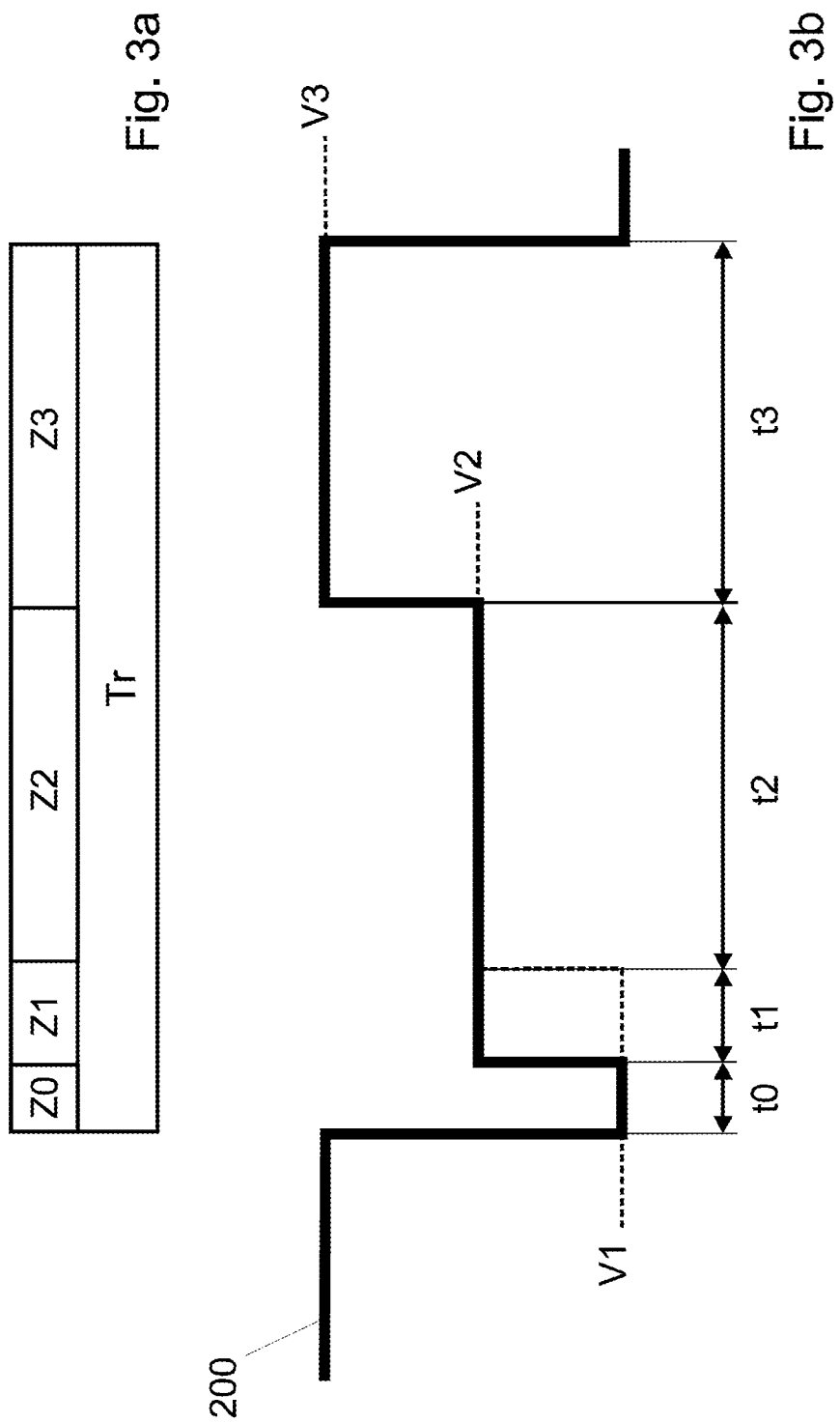

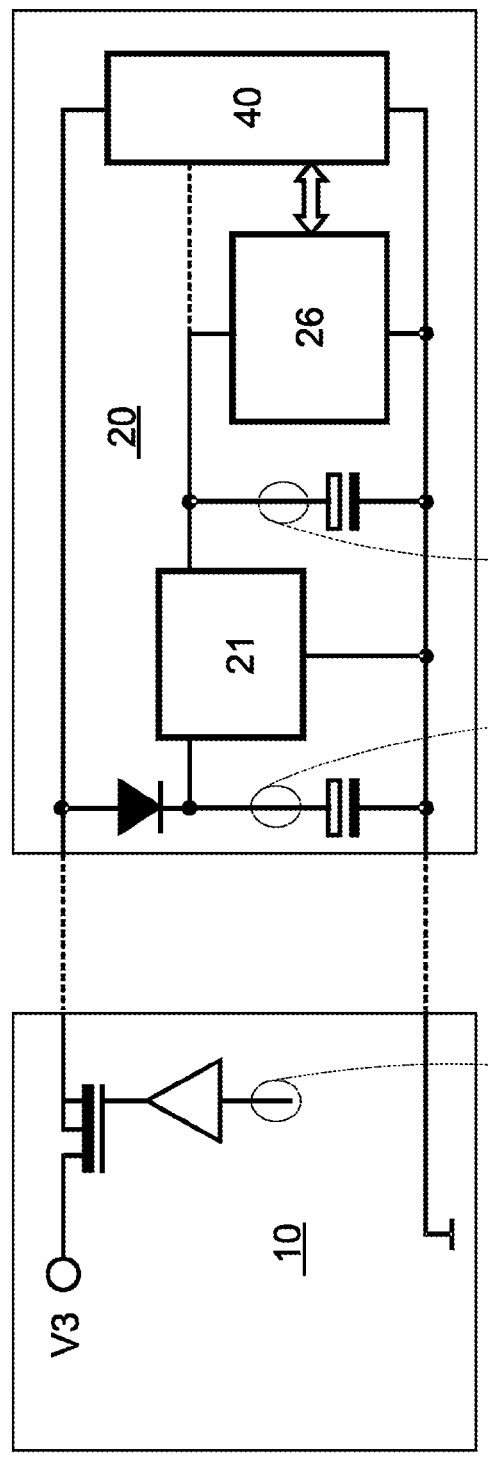

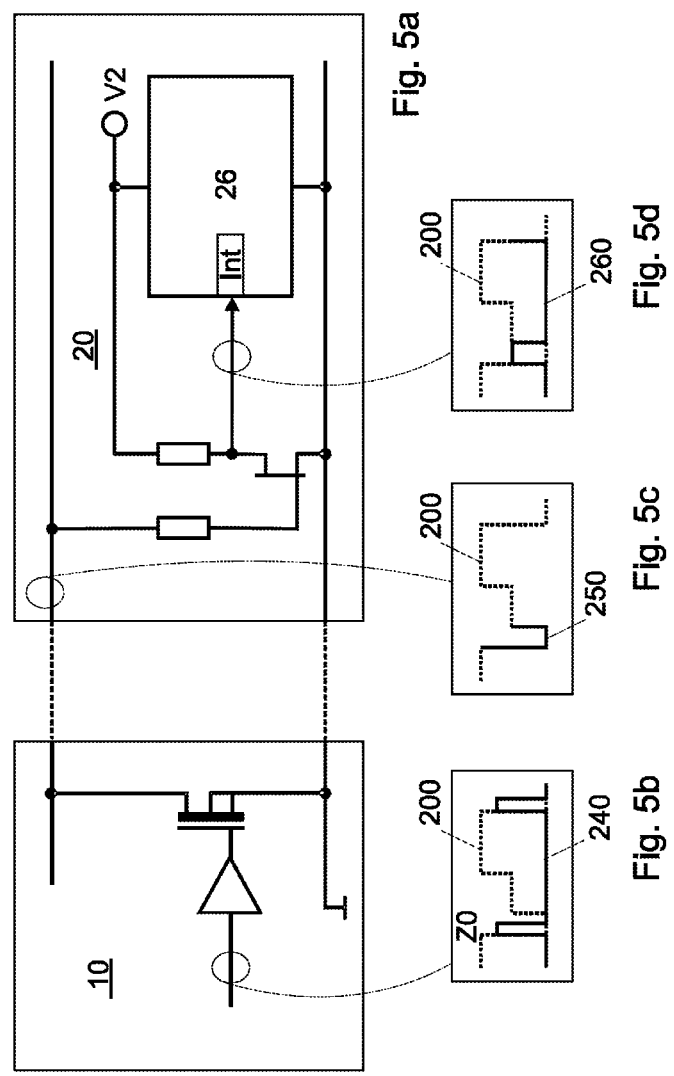

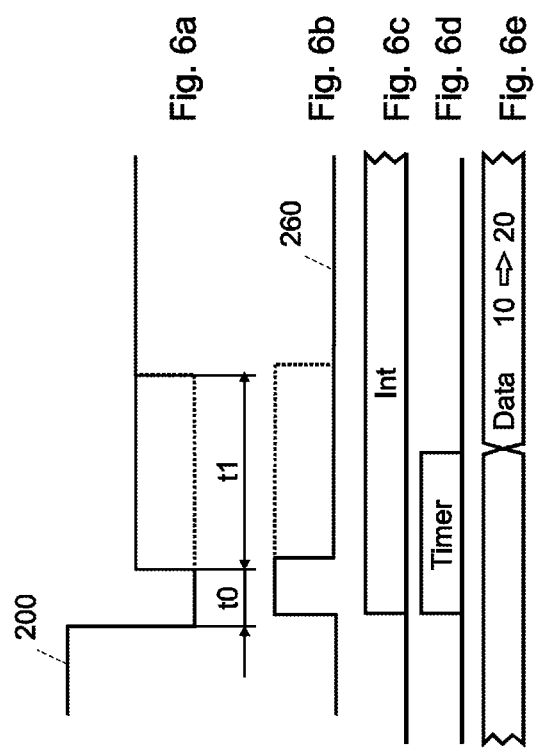

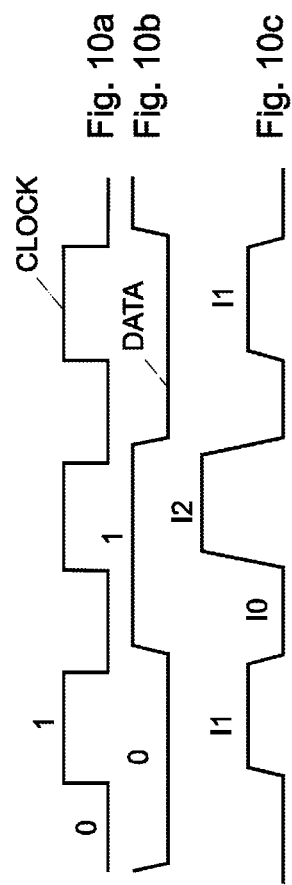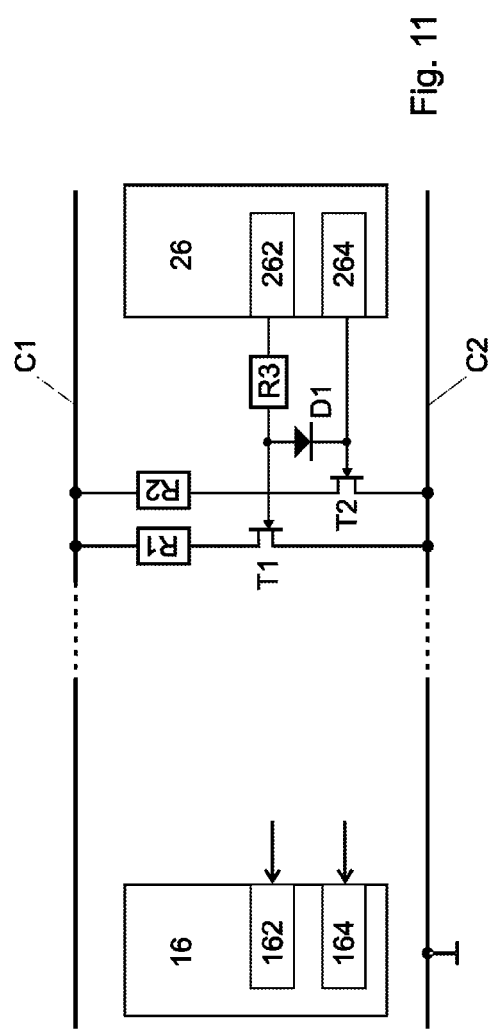

SURGICAL SYSTEM, IN PARTICULAR DENTAL SURGICAL SYSTEM

CROSS-REFERENCE TO RELATED APPLICATION

The present invention claims the priority of Swiss Patent Application CH20120000814, filed on Jun. 6, 2012 and published under the number CH706607, the content of which is incorporated here by reference.

TECHNICAL FIELD OF THE INVENTION

The present invention concerns a surgical system, in particular a dental system, comprising a dental or surgical instrument and a device for controlling the instrument.

BACKGROUND OF THE INVENTION

Surgical systems, in particular dental systems, comprise an instrument having a hand part, for example, a counter angle, which may be provided with a tool, for example a milling cutter—and a rotating motor that drives the tool. The hand part and the motor may be two separate pieces and interconnected by appropriate interfaces or may constitute a single piece. The instrument's controller device is often connected to the patient's chair and connected to the manual instrument by a flexible connection containing electric wires and tubes for passing air and water.

The rotary motors used in this type of hand-held instruments are more and more motors without commutators and without brushes, which have the advantage of being more robust and being capable of being sterilized completely. In order to avoid overheating of the instrument, which can be rotated at high speeds, for example up to 40,000 turns per minute or more, three-phase motors are preferable.

A rotary motor used in this type of hand-held instruments generally consists of a magnetically rotor with two poles and a stator winding with three windings. In order to set the coils on a precise angular position of the rotor for rotation which extend from 0 t/min, it is possible to equip the rotary motor with sensors, for example Hall effect sensors or magneto resistive sensors providing continuously rotor positions to the electronic control which is typically located at the exterior of the motor. Less precise solutions without sensors, are also known.

In the medical field, the allowable dimensions are very small and the bulky cables should be avoided. There is thus a need for new systems including hand tools providing mechanical and electronic miniaturization as well as an optimal reduction of the cables while preserving a maximum reliability.

The Document WO05037124, in the name of the Applicant, discloses a surgical system including a dental system, an embodiment of which is illustrated in FIG. 1. The illustrated system 1 includes a manual instrument 1 that includes a rotary motor M, two Hall effect sensors H1 and H2 arranged to determine at least one operating parameter of the motor M, and an electronic module 20.
The control device of the motor M comprises a first electronic module 10 and a flexible connection comprising the electrical conductors L1, L2, L3 and C0 for electrically connecting the first electronic module 10 with the second electronic module 20, and thus the control device to the instrument. The second electronic module 20 located inside the instrument processes output signals of the sensors H1 and H2, and transmits them to the controller device 10 through the flexible connector.

The electrical conductor L1 is the conductive phase of the motor M. From the high frequency point of view, this conductor corresponds to the neutral, for example the phase I.

The electrical conductor L2 is the conductive phase of the motor M, e.g. the phase II, on which is transmitted the drive component of the motor M, which is a low frequency signal, and the power supply high frequency component of the embedded microprocessor 26.

The electrical conductor L3 is the conductor of the phase of the motor M, for example the phase III, on which, the motor M drive component and the component of the data are transmitted, from the microprocessor 26 to the module 10.

The electrical conductor C0 is the power driver of an accessory 30, such as an incandescent lamp or LED, and the delivery driver of the information transmitted from the first electronic module 10 to the microprocessor 26. The information destined to the embedded microprocessor 26 in the instrument are encoded by frequency modulation on the electrical conductor C0.

Communications between the first electronic module 10 and the second electronic module 20, are mainly done by high frequency modulation of the conductors C0 and L3, in particular of the phase III of the motor. This has several disadvantages: it is in fact necessary to use lager volumes of magnetic elements, such as the two transformers 62 and 66 respectively associated with L3 and C0, and a demodulator 18, which rends the device expensive. The choice of the types of drivers of motor phases is accordingly limited by the fact that it should not interfere with high frequency signals. In addition, the system is sensitive to disruptions, in particular disruptions due to the existence of a common potential between four electrical conductors L1, L2, L3 and C0. Finally the system has a high cost.

Moreover, the use of the floating power supply 14 comprising an expensive PWM driver in the first electronic module 10, connected to the power supply 12 and allowing powering both the second electronic module 20, embedded in the manually actuated instrument, and the motor M trough the conductor L2, and which is potentially associated with the phase I (electrical conductor L1) of the motor M involves the use of a magnetic element, in particular the transformer 60 of lager volumes and therefore high cost.

U.S. Pat. No. 5,235,261 concerns a surgical system, in particular a dental system comprising a rotating motor for driving an instrument tool. This instrument does not have an electronic module inside the motor (second electronic module). This document does not describe an exchange of messages between a first and a second electronic module.

US2011266124 concerns a surgical system, in particular a dental system comprising an electronic circuit (second electronic module) inside the motor consisting of a fixed hardware performing predefined functions. In other words this second electronic module does not include a microprocessor. These functions are notified to the electronic management (first electronic module) of the system through six conductors. Each of these conductors carries a single signal, so that the number of signals (six) is equal to the number of conductors.

U.S. Pat. No. 5,538,423 relates to a method and a device for controlling operational parameters of a dental system, comprising an instrument having a commutator motor. This motor does not include switchable three phases, but only one variable voltage. The instrument does not have an electronic module inside the motor (second electronic module).

EP0688539 (Bien Air) concerns a dental handheld part comprising an electric driving and powering module of a lamp and an electromagnetic motor with no commutator whose connector comprises four power supply wires, i.e. three wires for the three motor coils and one wire for the lamp, the connection of the lamp taking advantage of the negative power supply line of one of the wires (or terminals). The lamp is thus connected to the power supply terminals of the motor, which can create interference problems and/or of electromagnetic compatibility (EM).

EP1753360 (Bien Air) discloses a flexible pipe connecting a dental instrument and a power supply comprising an additional power line via a dual function connector (conductive fluid and/or electricity). The additional conductor is insulated from conductors for powering a lamp and the motor and can be used to transmit a single signal.

There is therefore a need for a surgical system, especially dental system, capable of solving at least one of the disadvantages of the prior art.

There is also a need for a surgical system, especially a dental system, which is less bulky and cheaper than the known solutions.

There is also a need for a surgical system, especially a dental system, which is more reliable and does not present problems of interference and/or electromagnetic compatibility or EMC or having reduced interference problems compared to the known solutions.

BRIEF SUMMARY OF THE INVENTION

An aim of the present invention is to provide a surgical system in particular a dental system that is exempts of at least one of the drawbacks of the known systems.

Another aim of the invention is to propose a surgical system that is less bulky and cheaper than known solutions Another aim of the invention is to propose a surgical system in particular a dental system, which does not present the problems of interference and/or electromagnetic compatibility or does not presents reduced problems of interference and/or electromagnetic compatibility compared to known solutions.

According to the invention, these aims are achieved in particular by means of a surgical system, in particular a dental system having:
  A surgical instrument, in particular a dental instrument comprising a tool
  A control device of the instrument comprising a first electronic module.
The instrument comprises a rotary motor for driving the tool and a second electronic module.

The motor of the instrument is electrically supplied by the driver device through first electrical conductors dedicated to power supply of the motor. The instrument is supplied and/or electrically controllable by the control device through second electrical conductors which advantageously are distinct from the first conductors.

Advantageously, the system according to the invention further comprises a management module of the second electrical conductors for sending on the second electrical conductors a number of signals greater than the number of the second electrical conductors.

The system of the invention thus enables a complete separation between the power supply signals of the motor, of which the first electrical conductors are dedicated, and the driver and/or power supply signals of the instrument and/or accessory and/or synchronization signals between the electronic modules, which are associated with the second electrical conductors In a preferred embodiment, the second electrical conductors consists in two conductors and the management module of the second electrical conductor sends four signals on these second electrical conductors, in particular a power supply signal of the second electronic module, a power supply signal of an accessory, such as a lamp, a signal sent by the second electronic module to the first electronic module carrying at least information concerning the rotary motor and the general management information, and a signal sent by the first electronic module to the second electronic module carrying information concerning the command given by the first electronic module to the second electronic module. Thus the number of signals sent on the second electrical conductors (four) is greater than the number of second electrical conductors (two).

In a preferred embodiment the first electronic module comprises the management module. This management module may also be embedded in the second electronic module or be in both the first and the second electronic module.

Advantageously, the system according to the invention allows the removal of the magnetic elements and therefore a saving of space and of money because no demodulator is required in the control device for demodulating the power supply signals of the rotary motor of the instrument.

Advantageously, the system according to the invention does not have a floating power supply, or decoupling inductors, thus allowing space saving, reliability and achieving a more economical solution.

Moreover, the system according to the invention allows the use of digital communications with current loops which have a high degree of security and reliability.

According to the invention it is possible to have a high density of information and features on the second electrical conductors without using a high frequency modulation on the first electrical conductors.

In a preferred embodiment, the rotary motor of the system is a motor with no commutator. It is preferably tri-phases. In this variant, the first electrical conductors consist in three conductors, one for each of the three phases of the rotary motor.

In a preferred embodiment, the second electrical conductors consist in two conductors.

It is therefore possible to have a total of five electrical conductors, three dedicated exclusively for powering the rotary motor of the instrument and two, galvanically completely independent of the phases of the motor, that are dedicated to the control of the instrument and/or of the power supply of the instrument and/or accessories of the instrument and/or the synchronization between the electronic modules. The accessory of the instrument is preferably an incandescent lamp or a LED, for illuminating the work area, but may also be for example a pushbutton or a sensor.

Advantageously sent signals on the second electrical conductors comprise a synchronizing signal between a first electronic module and a second electronic module and at least two of the following signals:
  a power supply signal of the second electronic module
  a power supply signal of an accessory, for example a lamp
  a power supply signal of organs or auxiliary functions
  a second signal sent by the electronic module to the first electronic module carrying at least information relating to the rotary motor, these information comprising the instantaneous position of the rotor of the rotary motor, and general management information a signal sent by the first electronic module to the second electronic module carrying information relating to the command given by the electronic module to the second electronic module.

Advantageously, the signals on the second electrical conductors can be bidirectional: they may be sent by the first electronic module to the second electronic module and/or by the second electronic module to the first electronic module. In a preferred embodiment, the first electronic module send signals to the second electronic module during a first time interval, while the second electronic module sent signals to the first electronic module during a second time interval that is different from the first time interval. In other words, the signals in both directions are not sent simultaneously on the second conductors.

In an embodiment, the management module is arranged to send cycles of N periodic sequence on the second electrical conductors, N being a positive number.

In a preferred embodiment, N=4 and the first sequence corresponds to a clock signal sent by the first electronic module to the second electronic module the second sequence corresponds to a signal sent by the first electronic module to the second electronic module the third sequence corresponds to a signal sent by the second electronic module to the first electronic module The fourth sequence corresponds to a power supply signal of the second electronic module and/or the power supply signal of an accessory, for example a lamp, and/or a power supply signal of auxiliary organs or auxiliary functions.

Advantageously, the power supplying of the second electronic module by the first electronic module is provided only during the limited time period corresponding to the duration of the fourth sequence.

Advantageously, the communications from the second electronic module to the first electronic module on the second electrical conductors are digitals, in loop current, produced by activation of different currents.

In a variant, the first electronic module insures at least one of the following functions the servo control of the motor in general, in particular the three-phased power supply of the motor, in particular of the motor stator the interpretation and the management of information of the second electronic module The servo control of multiple interfaces and/or auxiliary organs allowing some additional features carried by the second electronic module, for example and not limited to the recognition of hand tools of the system the management of the synchronization with the second electronic module The communication of general management messages sent to the second electronic module addressed to auxiliary functions such as lamp.

In a variant, the second electronic module insures at least one of the following functions the calculation of the angle or the instantaneous position of the rotor of the motor of the instrument the communication with the first module, in particular concerning the instantaneous position of the motor rotor and messages of general management that are addressed the auxiliary functions the management of auxiliary functions, such as adjusting the intensity of the lamp.

The invention further relates to a method for a surgical system, in particular a dental system, comprising:

a surgical instrument, in particular a dental system, comprising a tool a control device of the instrument comprising a first electronic module the instrument comprising a rotary motor for driving the tool and a second electronic module the method comprising the supply of the rotary motor by the first electronic module of the control device through the first electrical conductors dedicated to the supply of the rotary motor;

the power supply and/or the control of the instrument by the first electronic module of the control device through the second electrical conductors distinct from the first electrical conductors, the second electrical conductors carrying a number of signals greater than the number of said second electrical conductors.

BRIEF DESCRIPTION OF THE DRAWINGS

Examples of implementation of the invention are indicated in the description illustrated by the appended figures in which:

FIG. 3a illustrates an example of an embodiment of a frame comprising four signal sequences sent to the second electrical conductors. FIG. 3b illustrates an example of a voltage signal corresponding to the sequences of FIG. 3a.

FIG. 4a illustrates an example of an embodiment of the hardware configuration for power supplying the second electronic module by the first electronic module.

FIGS. 4b-4d illustrate the voltage signal of FIG. 3b with respect to the signals in correspondence of the various nodes of the circuits of the hardware configuration of FIG. 4a.

FIG. 5a illustrates an example of an embodiment of the hardware configuration for synchronizing the second electronic module with the first electronic module, wherein the synchronization is performed by the first electronic module.

FIGS. 5b to 5d illustrate the voltage signal of FIG. 3b with respect to the signals in correspondence of the various nodes of the circuits of the hardware configuration of FIG. 5a.

FIGS. 6a to 6e illustrate an example of the communication signals sent by the first electronic module to the second electronic module.

FIG. 7 illustrates an embodiment of a message sent by the first electronic module to the second electronic module.

FIGS. 10a to 10c illustrate an embodiment of the relationship between the clock signal, the data signal and the current flowing on the second electrical conductors C1, C2, according to the invention.

FIG. 11 illustrates an embodiment of the communication of the second electronic module with the first electronic module.

DETAILED DESCRIPTION OF POSSIBLE EMBODIMENTS OF THE INVENTION

Figure 2:
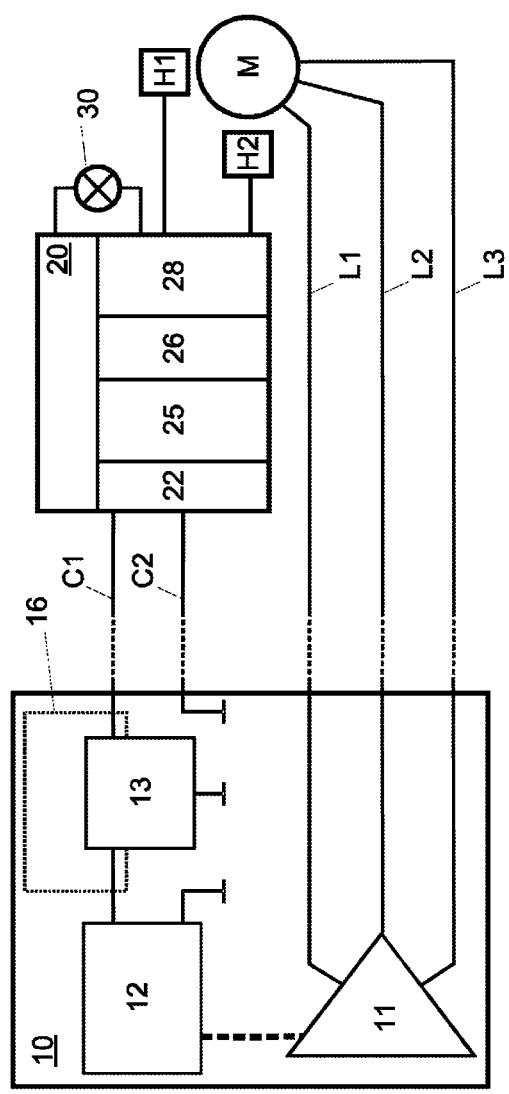
FIG. 2 illustrates a block diagram of an embodiment of the surgical system, in particular dental system, according to the invention.

FIG. 2 illustrates a block diagram of an embodiment of the surgical system, in particular the dental system, according to the invention. This system comprises:

a surgical instrument, in particular a dental instrument with a rotary motor M for driving a tool, for example a cutter, and a second electronic module 20 in the instrument a control device of the instrument comprising a first module electronic 10.

The motor M preferably includes a hanging or turbinate (not shown) for receiving a hand part not shown.

The instrument is preferably connected to a first electronic module 10 by a flexible connection, for example a flexible pipe (not shown) attached to the motor M. The instrument is supplied for example in water, air and in electricity by this pipe.

In the case of the dental instrument of FIG. 2, the pipe comprises five electrical conductors, including three first electrical conductors L1, L2 and L3, and two second electrical conductors C1 and C2.

The motor M of the instrument is electrically powered by the control device through the first electrical conductors L1 to L3 that is dedicated to supplying the motor. The instrument is powered and electrically controlled by the control device via the second electrical conductors C1 to C2 that are advantageously distinct from the first conductors.

In a preferred embodiment, the rotary motor M of the system according to the invention is without commutator. It is preferably three-phased. In this variant, illustrated in FIG. 2, the first electrical conductors L1 to L3 are three conductors, one conductor for each of the three phases of the rotary motor.

In the variant of FIG. 2, the second electrical conductors are two conductors, C1 and C2.

It is therefore possible to have five total electrical conductors, three (L1 to L3) dedicated exclusively for supplying the rotary motor of the instrument and two (C1 and C2) galvanically completely independent of motor's phases, dedicated to the control and the supply of the instrument. The accessory of the instrument is preferably a light bulb 30, for example a LED, for illuminating the work area, but any other types may also be envisaged, for example a pushbutton or a sensor.

The flexible connector connecting the dental instrument to the control device may also comprise (non-illustrated) pipes for the passage of air and/or liquid. The pipes for the passage of air and/or liquid. preferably comprise a water supply line for a spray and/or also a cooling air supply line for cooling the motor M and/or an air return line.

The motor M is, for example a motor without brushes including a rotor and three coils. As discussed, it may be for example a three-phased motor with no commutator comprising three stator windings, for example star-assembled.

The rotary motor M may further comprise two sensors H1, H2 for determining at least one motor operating parameter. The sensors H1, H2 are, for example analog Hall effect sensors or magneto-resistive sensors for determining the instantaneous angular position of the motor's rotor. As illustrated in FIG. 2, the two sensors H1, H2 are preferably arranged in order to form an angle of 90° between them.

Advantageously, the system according to the invention also comprises a management module 13 which in the illustrated example is in the first electronic module 10, to send to the second electrical conductors C1, C2 a number of signals greater than the number of the second electrical conductors C1, C2

In other words, the management module 13 manages the temporal sequences between electronic modules 10, 20 by performing a sort of time multiplexing of several signals on the second electrical conductors C1 and C2, wherein these signals are bidirectional: some are sent by the first electronic module 10 to the second module 20, others sent by the second electronic module 20 to the first module 10. As discussed, in a preferred embodiment, the signals in both directions are not simultaneous.

The system of the invention thus enables a complete separation between the supply signals of the motor, to which the first electrical conductors L1 to L3 are dedicated, and the clock and/or control and/or supply signals of the instrument and/or accessory signals of the instrument, associated with the second electrical conductors C1 and C2.

Advantageously, according to the invention, the system allows the removal of the magnetic elements and therefore a substantial saving in space and money, because the demodulator in the control device, which allows a demodulation of supply signals of the rotary motor M of the instrument from other signals, is no longer necessary.

The first electronic module 10 includes a microprocessor 16, a power supply 12, a control module 11 of the first electrical conductors L1 to L3 and the management module 13 of the second electrical conductors C1 and C2.

The second electronic module 20 comprises a microprocessor 26, a supply module 22, an acquisition module 28 of the positions of the rotary motor M and a module for managing digital communications 25 on the second electrical conductors C1 and C2 in a continuous current loop, as discussed below.

In the illustrated embodiment, the second electronic module 20 is connected to an accessory 30 and to two position sensors H1 and H2, for example, two Hall effect sensors.

Figure 1:
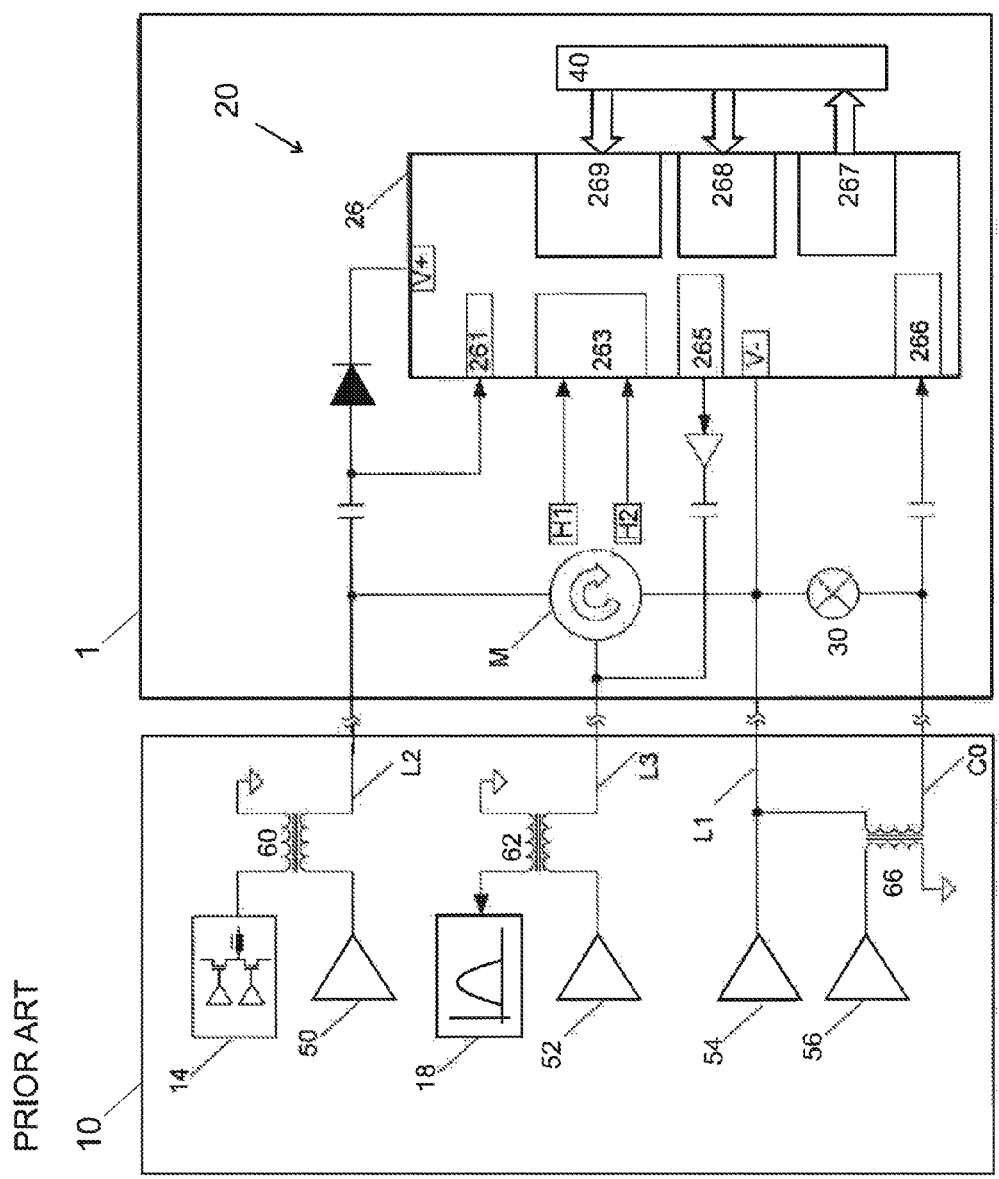
FIG. 1 illustrates a block diagram of a prior-art embodiment of a surgical system, in particular a known dental system.

Advantageously, the system according to the invention has no floating power supply 14 of FIG. 1, and therefore no decoupling coils, which allows space saving, reliability and achieving a more economical solution.

Advantageously, the system according to the invention does not have the demodulator 18 of FIG. 1, since it is no longer necessary to transmit the communication signals between the first and second electronic modules 10, 20 using a high modulation frequency: in fact, the presence of the second electrical conductors C1 C2 makes unnecessary the achievement of this modulation on the conductors L1 to L3.

The second electrical conductors C1 and C2 can work by cycles of N periodic sequences, N being a positive number. N sequences constitute a frame Tr. In the variant illustrated in FIG. 3a, N=4 and the sequences are numbered from Z0 to Z3. FIG. 3b illustrates an example of a voltage signal 200 corresponding to the frame of FIG. 3a.

On the second electrical conductors C1 and C2, the signal for synchronization between the first electronic module 10 and the second electronic module 20 and at least two of the following signals are multiplexed:

the power supply signal of the second electronic module 20 the power supply signal of an accessory, for example a lamp the power supply signal of auxiliary organs or auxiliary functions the power signal from the second electronic module 20 to the first electronic module 10: this signal is a high speed signal, meaning that at least 500 kBauds, and carries information relating to the rotary motor M the signal sent by the first electronic module 10 to the second electronic module 20: this signal is a medium speed signal, meaning that at least 4800 Bauds, and carries information regarding the command given by the first electronic module to the second electronic module 20.

In the variation of FIGS. 3a and 3b, the sequence Z0 corresponds to a voltage signal V1, for example V1=0 V, which has a time duration t0, for example t0=2 µs. This signal is a clock signal sent by the first electronic module 10 to the second electronic module 20.

The sequence Z1 corresponds to a voltage signal V2, for example V2=5 V, which has a time duration t1, for example t1=8 µs. In this example, this signal is sent by the first electronic module 10 to the second electronic module 20: this signal is a medium speed signal, meaning that at least 4800 Bauds, and carries information regarding the command given by the first electronic module 10 to the second electronic module 20.

The sequence Z2 corresponds to of a voltage signal V2, for example V2=5 V, which has a time duration t2, for example t2=50 µs. This signal, in this example, is sent by the second electronic module 20 to the first electronic module 10: this signal is a high speed signal, meaning that at least 500 Kbauds, and carries information regarding the position of the rotor of the motor M.

The sequence Z3 corresponds to a voltage signal V3, for example V3=12 V, which has a time duration t3, for example t3=60 µs. This signal is the power supply signal of the second electronic module 20 and/or the power supply signal of an accessory, for example a lamp 30 and/or the power supply signal of organs or auxiliary functions.

The given voltage values V1 to V3 and the given time slots t0 to t3 are not exhaustive and may be modified by one skilled person according to the applications Both the sequences shown in FIG. 3a are also indicative and it is for instance possible to work in cycles of N periodic sequences, N being a number different than four. It is also possible to use the frame Tr, shown in FIG. 3a, with a different order of the sequences, for example Z2, Z3, Z0 and Z1.

In a preferred embodiment the sequence Z3 corresponds to the supply of the second electronic module 20 by the first electronic module 10. This supply is carried out only during the time duration t3, which in a preferred embodiment is half of the total time duration of the frame Tr, corresponding to t0+t1+t2+t3. During the remaining time, the second electronic module 20 must rely on its own energy storage.

Sequence Z3

An embodiment of the hardware configuration of the supply of the second electronic module 20 by the first electronic module 10 is described in FIG. 4a.

As illustrated in FIG. 4b, the energy consumption of the second electronic module 20 is performed only during the time duration of the sequence Z3. One or more capacitors of the second electronic module 20 allows an accumulation of energy as can be seen in FIG. 4c. The stabilizer 21 allows having a constant voltage signal and equal to V2, for example V2=5V, as can be seen in FIG. 4d, reference 230.

Auxiliary organs 40 can be supplied either by the stabilizer 21 in the case of low consumption, either directly on the second electrical conductors C1 and C2 while assuming that the energy consumption stays within the confine zone Z3.

Sequence Z0

In a preferred embodiment, the two electronic modules 10 and 20 are synchronized. In a preferred embodiment, the synchronizer unit is the first electronic module 10 (master) and synchronized unit is the second electronic module 20 (slave).

The synchronization signal is preferably generated by the first electronic module 10 (master) at the beginning of the cycle, so in correspondence to the sequence Z0, by a reset of the second electrical conductors C1 and C2. This zero potential is detected by the second electronic module 20, which causes an "interrupt" signal on the embedded microprocessor 26, as shown in FIG. 5a.

To the clock signal 240 generated by the first electronic unit 10 and shown in FIG. 5b corresponds thus a reset 250 of the second electrical conductors, shown in FIG. 5c. The "interrupt" signal 260, shown in FIG. 5d, occurs at the moment when the tension of the second electrical conductors falls to zero. In this way the synchronization between the first and the second module is not dependent on the duration of the clock signal 240.

Sequence Z1

As discussed, in a preferred embodiment the signals transmitted by the first electronic module 10 toward the second electronic module 20 (communication 10→20) correspond to the sequence Z1 in FIG. 3a, which has a duration t1.

As discussed, these signals are mid-speed signals, meaning that at least 4800 baud, which carry information about the command sent by the first electronic module 10 to the second electronic module 20. These signals are therefore general management API-type (<<Application Programming Interface>>) signals, not directly related to the rotation of the rotary motor M, but addressed primarily to auxiliary functions, such as lamp 30.

The microprocessor 26 of the second electronic module 20, as soon as the reception of the "interrupt" synchronization signal 260, shown in FIG. 6b, which causes an interruption state << Int>> in the microprocessor 26 of the second electronic module 20, shown in FIG. 6c, commits a "timer" signal shown in FIG. 6d. This signal has a duration of a few µs, for example 6 µs.

At the end of this timer signal, the microprocessor 26 of the second electronic module 20 determines the nature of the data received. A data "0" corresponds to a synchronizing signal 250 of short duration, for example 2 µs, and a data "1" corresponds to a synchronizing signal 250 of long duration, for example 10 µs.

The digital data messages sent by the first electronic module 10 to the second module 20 thus have the same frequency as the frame Tr of the second electrical conductors.

If the total duration of the frame Tr, illustrated in FIG. 3b and corresponding to t0+t1+t2+t3, is for example equals to 120 µs, the transmission speed of these messages is 8.33

KBauds. This rate, although relatively slow, is sufficient as orders for the overall management given to the motor M do not require instantaneous execution.

The data transmission protocol of the signals sent from the first electronic module 10 to the second electronic module 20 may for example be the API protocol illustrated in FIG. 7 wherein:

H [char] is the beginning of the message
FUNC [Byte] is the codification of the message according to a table
ADDR [Byte] is the address register
DATAi [Byte] is the string of bytes
CRC [Word] is an error control code, for example based on a polynomial algorithm.

Sequence Z2

As discussed, the sequence Z2 corresponds to a signal sent by the second electronic module 20 to the first electronic module 10.

This signal carries at least information concerning the rotary motor M, these information comprising the instantaneous rotary position of the rotor of the motor M. This signal carries information that are similar to the general management information sent by the first electronic module 10 to the second electronic module 20.

Since the messages sent by the second electronic module 20 to the first electronic module 10 carrier the instantaneous position of the rotor of the rotary brushless motor M, position which must be known at all times by the first electronic module 10 to ensure rotation of the motor M, these messages require a higher transmission speed than the messages sent by the first electronic module 10 to the second electronic module 20.

Figure 8:
FIG. 8 illustrates an embodiment of a message sent by the second electronic module to the first electronic module.

These communications occur during the sequence Z2 by a message which, in a preferred embodiment, is composed of 24 bits. An example of such a message is illustrated in FIG. 8, where Sb ("Start bit") is the first bit
GP MSG is a general management message, whose protocol may be different depending on the applications; in the illustrated variant, the message is composed of four bits
DPA (Angular Line of Position) is the instantaneous position of the rotor of the rotary motor M; in a preferred embodiment, 360° correspond to 4096 angle unit
CRC-8 ("Cyclic Redundancy Check") is a normalized check polynomial, for instance CRC8 CCITT $x^8+x^2+x+1$
Eb ("End bit") is the last bit.

As discussed, the sequence Z2 does not generate energy consumption by the second electronic module 20: it is thus possible to use energy only when transferring information. For example, the bit "0" may correspond to the absence of energy consumption, including current consumption, while the bit "1" may correspond to a predetermined current consumption, for example and not limited to a consumption of 50 mA.

Since there are preferably a synchronous communication between the microprocessor 16 of the first electronic module 10 and the microprocessor 26 of the second electronic module 20, a clock signal must be associated with the data to indicate the time of validity of the transmitted data to the receptor, in particular to the first electronic module 10. Other solutions with no "clock" signal, for example by using the fixed value of a first bit of a sequence, may also be considered.

Figure 9:
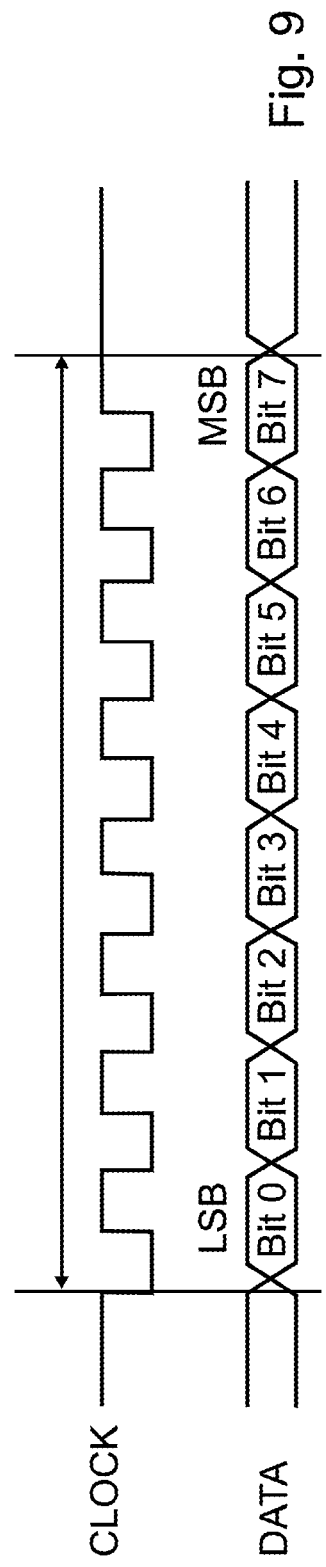
FIG. 9 illustrates an example of the process of peripherals SCI ("Serial Communications Interface") of the microprocessors of the first and the second electronic modules in a synchronous transmission mode.

FIG. 9 illustrates an example of the process of the peripheral SCI ("Serial Communications Interface") of the microprocessors 16 and 26 in a synchronous transmission mode. The clock signal defines, in the case of a transmission which is not continuous, a time window, indicated in FIG. 9 by the arrow, which allows to consider only data bits or "data" falling in this window, e.g. bits 0 to 7 of the illustrated example.

FIGS. 10a to 10c illustrate an embodiment of the relationship between the clock, the data and the current on the second electrical conductors C1, C2 according to an embodiment of the invention.

During the sequence Z2 the state "0" of the clock signal, shown in FIG. 10a, can prohibit the consumption through the second electrical conductors and the state "1" can cause two different current consumptions I1, I2, shown in the FIG. 10c, according to the state of the corresponding data, shown in FIG. 10b.

Therefore, if the clock signal is zero, the power consumption is always I0, which in a preferred embodiment corresponds to 0 mA.

If the clock signal is in the state "1", for a data bit equals to zero, the current consumption by the second electronic module 20 is I1, in a preferred embodiment I1=25 mA.

If the clock signal is in the state "1", for a data bit equals to one, the current consumption by the second electronic module 20 is I2, in a preferred embodiment I2=50 mA.

FIG. 11 illustrates schematically one embodiment of communication of the second electronic module with the first electronic module.

If the clock signal 264 output from the microprocessor 26 of the second module 20 is in the state "0", diode D1 prevents transistor T1, T2 to be in conduction. If it is "1" and the data 262 to "0", only the transistor T2 conducts and causes a current consumption of V2/R2. In a variant V2/R2=25 mA. On the other hand, if the clock signal 264 and the data 262 are simultaneously at "1", T1 and T2 are conducting. In this case, the current consumption is V2/R1+V2/R2. In a variant, V2/R1+V2/R2=50 mA.

Transmissions by current consumption from the second electronic module 20 to the first electronic module 10 thus take the characteristics of the FIG. 10c.

Figure 12:
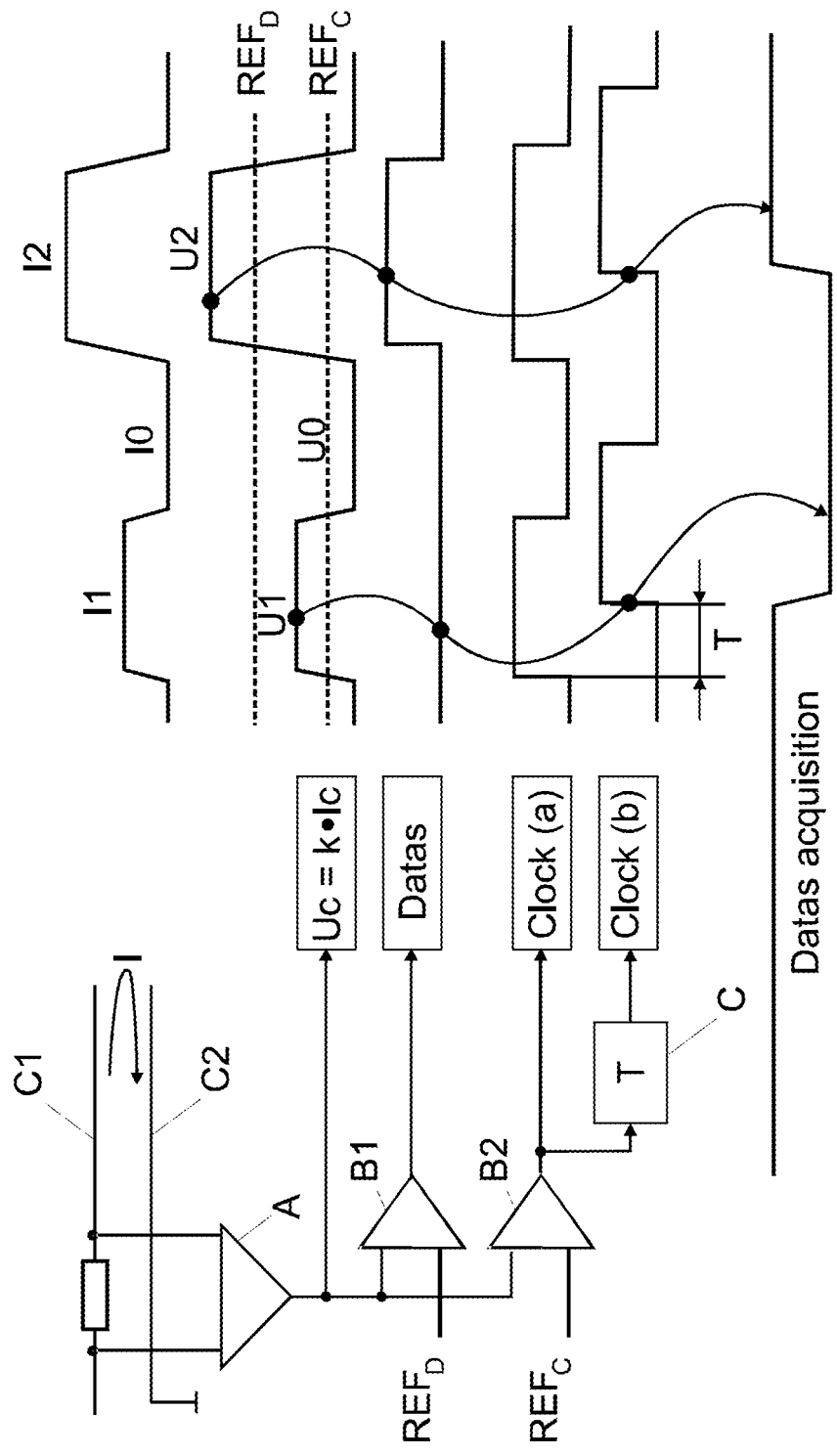
FIG. 12 illustrates an example of how the first electronic module reconstructs the clock signal and the data in a readable configuration by the microprocessor.

FIG. 12 illustrates an example of reconstruction of clock signals and data from the first electronic module 10 in a readable configuration by its microprocessor 16.

The differential amplifier A converts the current variations I of the second electrical conductors C1, C2 in proportional voltage variations Uc=k·Ic referenced to the zero potential (ground). From Uc, a first trigger B1 can extract the state data "1" when Uc>$REF_D$ and a second trigger B2 reforms the signal clock (a) when Uc>$REF_C$.

In order to have a correct acquisition of data by the microprocessor 16, a time switch C generates a clock signal (b) by delaying it clock (a). A time delay less than 1 μs, for example delay of about 100 ns, is enough. In this way the clock acts on a stable state of the data.

Figure 13:
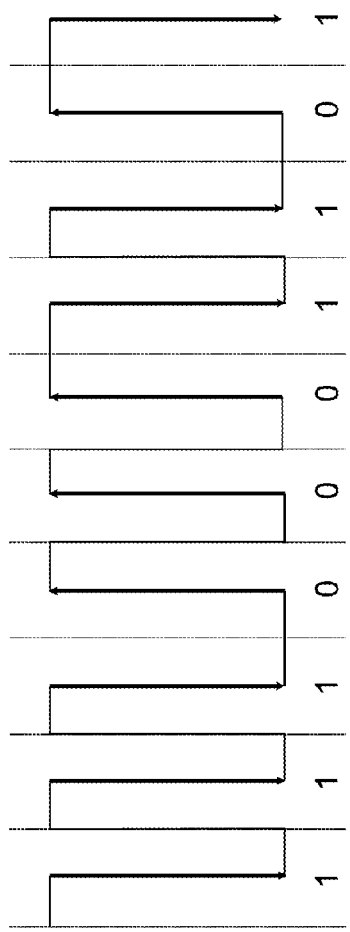
FIG. 13 illustrates an example of arrangement of the synchronous transmission in which the combination clock-data signal is a mono-signal ("Manchester code").

In the shown examples in FIGS. 9 to 12, the clock and the data are two separate signals, which allows simple encoding and decoding of signals. In another variant, it is possible to have another arrangement of synchronous transmission in which the combination clock-data is a mono signal. An example is given by the "Manchester code" shown in FIG. 13.

Figure 14:
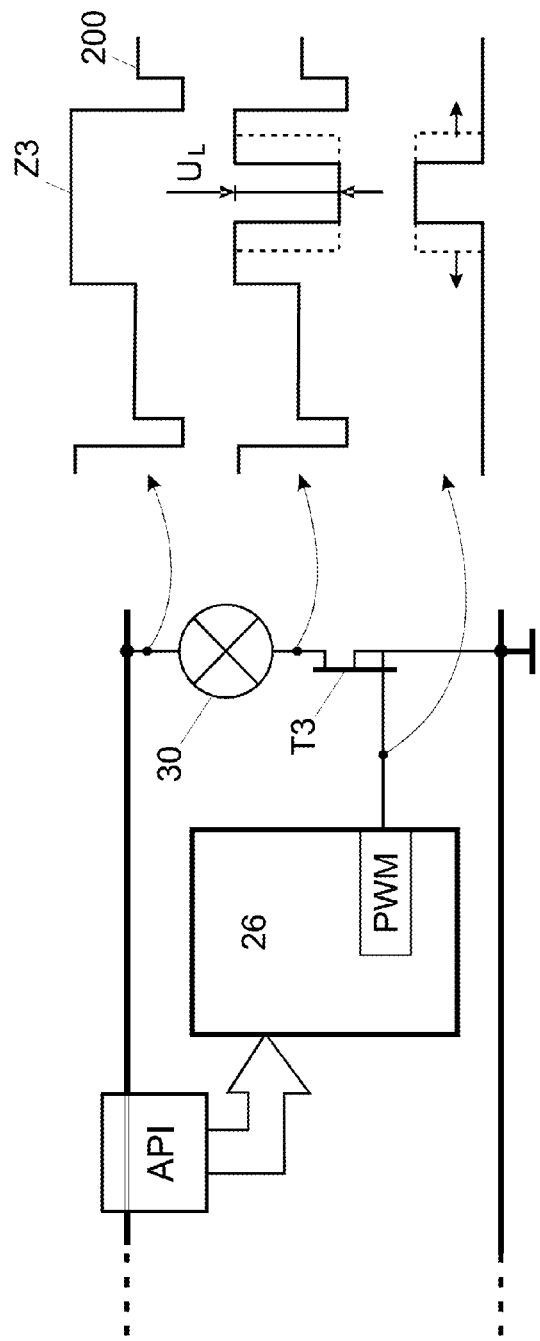
FIG. 14 illustrates an example of the PWM technique for supplying an accessory such as a lamp.

The management of an accessory, such as a lamp 30, is controlled by the microcontroller 26 of the electronic module 20 according to API commands given by the first electronic module 10, as illustrated in FIG. 14.

In a variant, the lamp supply 30 is based on the PWM technique ("Pulse Width Modulation") generated by the microcontroller 26 of the second electronic module 20.

As discussed, in a preferred embodiment, the supply of the lamp 30 is only allowed during the sequence Z3: the frequency of PWM is equals to the cycles of the second electrical conductors and the opening duration of PWM ranges from 0% to 50%, or generally equals to an opening time t3.

According to the lamp voltage $U_L$ requested by the command API, the microcontroller 26 of the second electronic control module 20 controls an opening of the transistor T3 with equivalent duration. In one example, the duty cycle is maximum 50% and the voltage V2 during Z3 is 12 Vdc, the maximum lamp voltage is thus 6 Vdc.

Possible auxiliary organs can be supplied during the sequence Z3 in the same manner as the lamp 30, for example by a second PWM, or, if their consumption is low, for example less than 100 mA, in the same way that the second electronic module 20.

Figure 15:
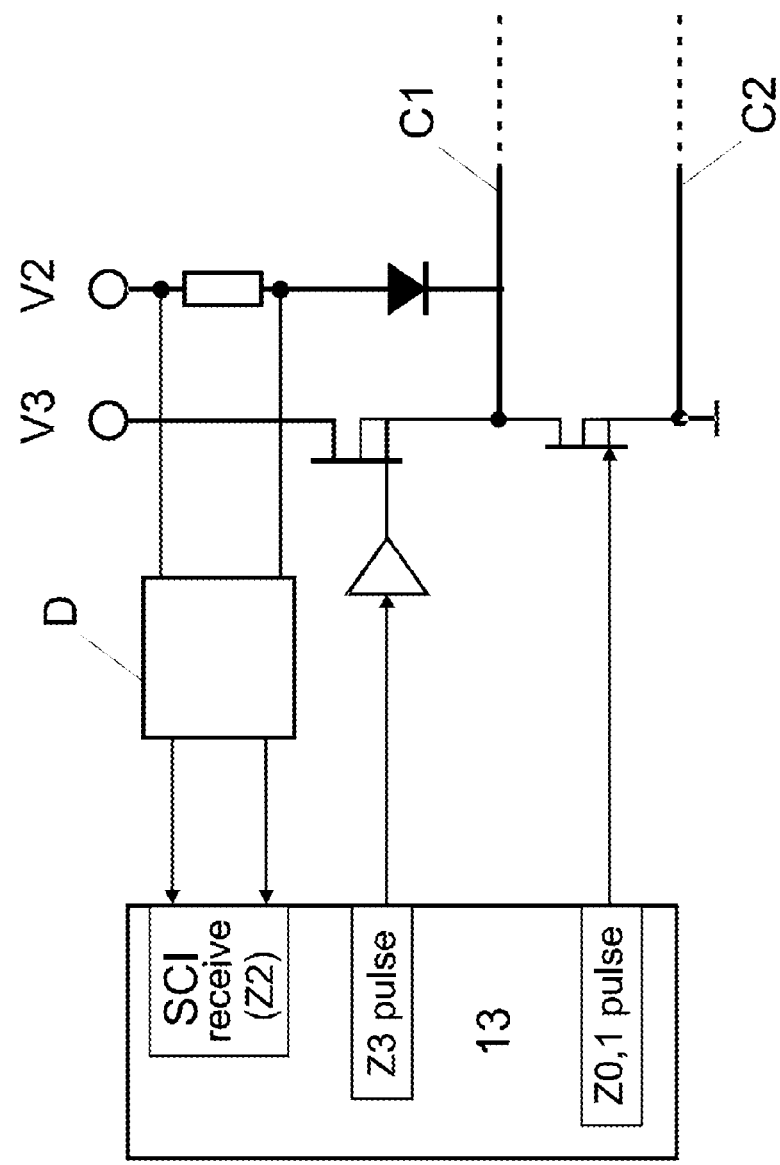
FIG. 15 illustrates an example of the drivers of the first electronic module that activate different states of the second electrical conductors.

FIG. 15 illustrates an embodiment of the management module of the second electrical conductors that activates the different states of the second conductors C1, C2. The reference D indicates the decoder of message sent by the second module 20 to the first 10 during the sequence Z2.

Figure 16:
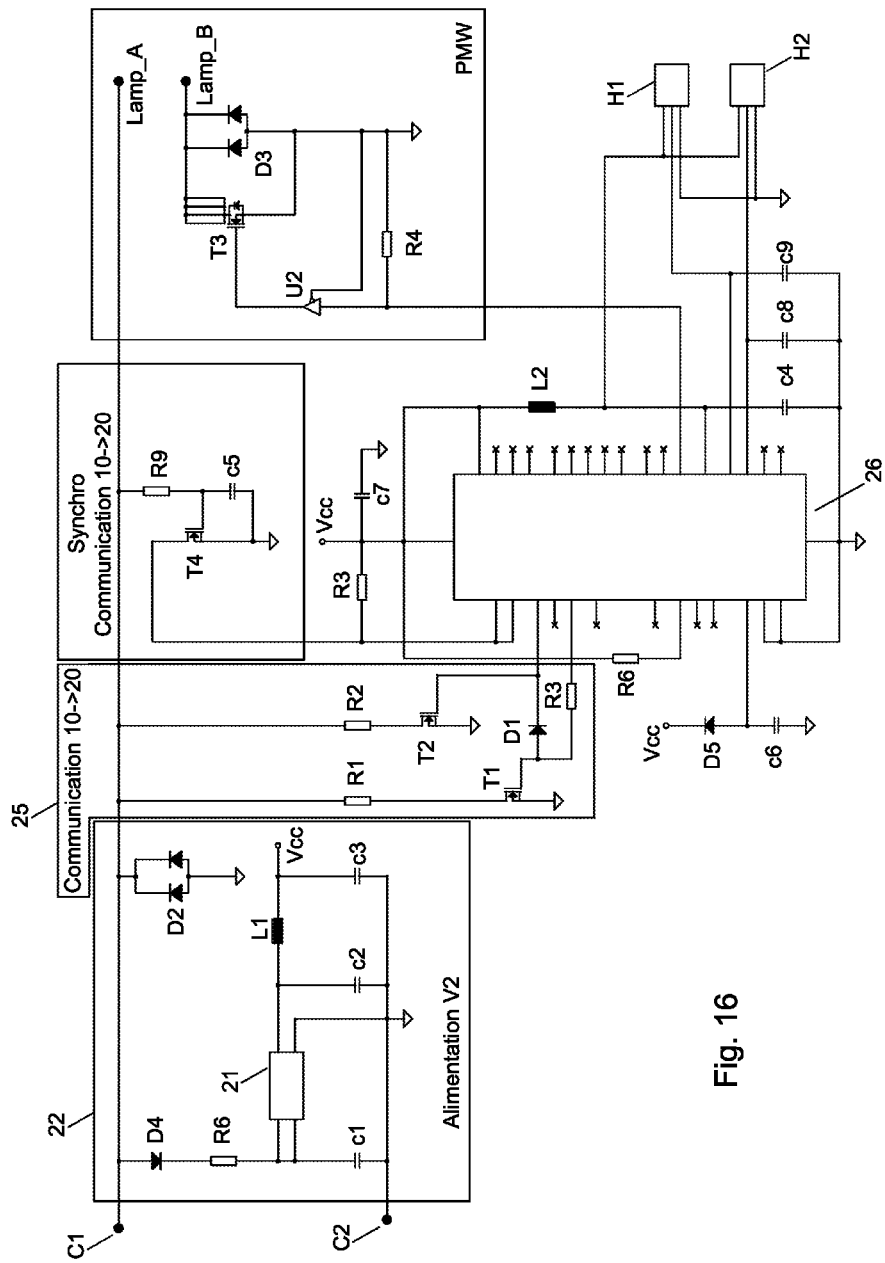
FIG. 16 illustrates an example of a second embodiment of the electronic module and the rotary motor.

FIG. 16 illustrates an example of an embodiment of the second electronic module 20 and the rotary motor M.

Figure 17:
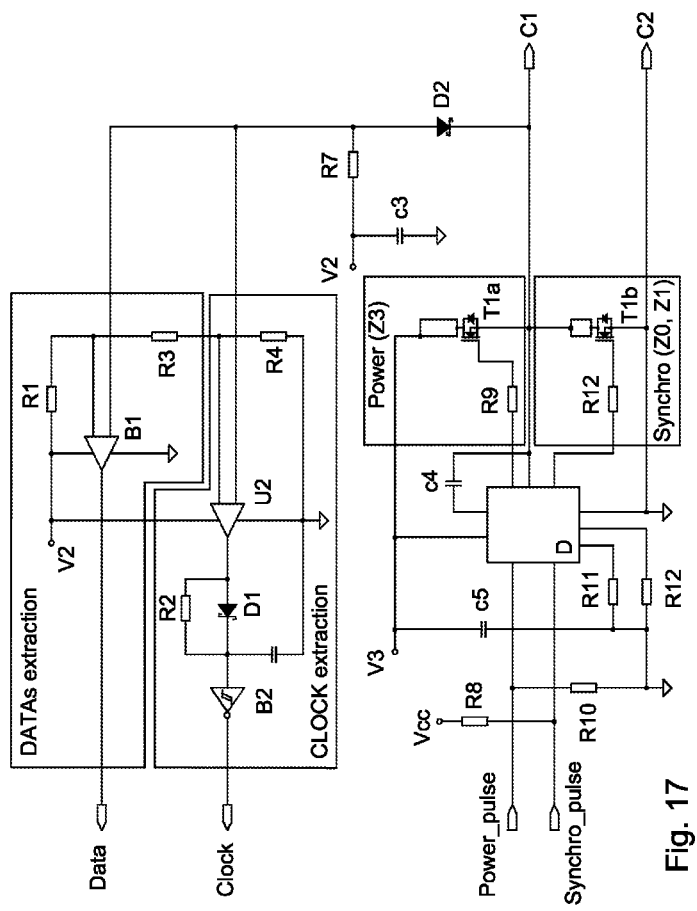
FIG. 17 illustrates an example of an embodiment of the drivers of the first electronic module.

FIG. 17 illustrates an example of an embodiment of the drivers of the first electronic module 10.

The invention also concerns a method for surgical system, in particular a dental system, comprising:
- a surgical instrument, in particular a dental system, comprising a tool
- a control device to said instrument comprising a first electronic module (10)
- said instrument comprising a rotary motor (M) for driving the tool and a second electronic module (20)
- said method comprising
  - the power supply of said rotary motor (M) by said first electronic module (10) of said control device through the first electrical conductors (L1, L2, L3) dedicated to the supply of said rotary motor (M);
  - the power supply and/or the control of said control device by said first electronic module (10) of said control device through the second electrical conductors (C1, C2) distinct from the first electrical conductors (L1, L2, L3),
- said second electrical conductors (C1, C2) carrying a number of signals greater than the number of said second electrical conductors (C1, C2).

REFERENCE NUMBERS USED ON THE DRAWINGS

1 Instrument
10 First electronic module (in the control device)
11 Drivers
12 Power supply module of the first electronic module
13 Management module of the second electrical conductors
14 Floating power supply
16 Microprocessor of the first electronic module
18 Demodulator
20 Second driver device (in the surgical instrument, in particular the dental instrument)
21 Voltage regulator
22 Power supply module of the second electronic module
24 High frequency communication module
25 Digital communication management module <<current loop>>
26 Microprocessor of the second electronic module
28 Acquisition module of the position of the rotor's motor
30 Accessory, for example lamp
40 Auxiliary organs
50 Amplifier
52 Amplifier
54 Amplifier
56 Amplifier
60 Transformer
62 Transformer
66 Transformer
162 Module for the reception of the data sent by the second electronic module
164 Module for the reception of the <<clock>> signal sent by the second electronic module
200 Voltage signal corresponding to a frame
210 Signal providing cyclical energy in correspondence of sequence Z3
220 Storage energy signal in the second electronic module
230 Voltage signal equals to V2
240 Clock signal in the first electronic module
250 Clock signal transmitted to the second electronic module
260 Interrupt Signal
261 Synchro
262 Module for sending data to the first electronic module
263 Analog/Digital
264 Module for sending the clock signal to the first electronic module
265 Data outputs
266 Data Inputs
267 Auxiliary digital outputs
268 Auxiliary digital inputs
299 Auxiliary analog/digital
L1 First electrical conductor
L2 First electrical conductor
L3 First electrical conductor
C0 Electrical conductor for lamp supply
C1 second electrical conductor
C2 Second electrical conductor
M Rotary motor
H1 First Hall effect sensor
H2 Second Hall effect sensor
Z0 First sequence
Z1 Second sequence
Z2 Third sequence
Z3 Fourth sequence
Tr Frame
V1 First voltage value
V2 Second voltage value
V3 Third voltage value
t0 Time duration of the first sequence
t1 Time duration of the second sequence
t2 Time duration of the third sequence
t3 Time duration of the fourth sequence
I0 First current value
I1 Second current value
I2 Third current value
U1 Voltage value proportional to I1
U2 Voltage value proportional to I2
U3 Voltage value proportional to resistance I3
R1 Resistance
R2 Resistance
R3 Resistance
D1 Diode T1 Transistor
T2 Transistor
T3 Transistor
A Differential amplifier
B1 First trigger
B2 Second trigger
C Temporizer
$U_L$ Voltage of the lamp
D Decoder

The invention claimed is:

1. Surgical system comprising:
a surgical instrument, comprising a tool;
a device for controlling said surgical instrument, said device comprising a first electronic module,
said instrument comprising a rotary motor for driving the tool and a second electronic module,
said rotary motor of the instrument being electrically powered by said first electronic module of said device through first electrical conductors, said first electrical conductors being dedicated to supply said rotary motor, and
said second electronic module and/or said tool being powered and/or electrically controlled by said first electronic module of said device only through second electrical conductors, said second electrical conductors being distinct from the first electrical conductors; and
a management unit of said second electrical conductors in the first electronic module or in the second electronic module, for sending on said second electrical conductors a number of signals greater than the number of said second electrical conductors.

2. The system according to claim 1, the number of said second electrical conductors being equal to two.

3. The system according to claim 2, said signals sent on said second electrical conductors comprising a clock signal for synchronizing said first electronic module and said second electronic module, and including at least two of the following signals:
a power supply signal of said second electronic module;
a power supply signal of an accessory;
a power supply signal of auxiliary organs or of auxiliary functions;
a second signal sent by said second electronic module to said first electronic module, carrying at least information relating to said rotary motor, this information comprising the instantaneous position of the rotor of said rotary motor, and general management information;
a signal sent by said first electronic module to said second electronic module carrying information relating to a command given by said electronic module to the second electronic module.

4. The system according to claim 3, said signal sent by said second electronic module to said first electronic module having a number of symbols per second of at least 500 kBauds.

5. The system, according to claim 3, said signal sent by said first electronic module to said second electronic module having a number of symbols per second of at least 4800 Bauds.

6. The system according to claim 1, said management unit being arranged to send on said second electrical conductors cycles of N periodic sequences, N being a positive number.

7. The system according to claim 6,
N being equal to four;
a first sequence corresponding to a clock signal between said first electronic module and said second electronic module;
a second sequence corresponding to said signal sent by said first electronic module to said second electronic module;
a third sequence corresponding to said signal sent by said second electronic module to said first electronic module; and
a fourth sequence corresponding to the power supply signal of said second electronic module signal and/or to the power supply signal of an accessory and/or to the power supply signal of auxiliary organs or auxiliary functions.

8. The system according to claim 7, said fourth sequence having a time duration of an half of the sum of the time durations of all four sequences.

9. The system according to claim 7, the power supply of said second electronic module by said first electronic module being provided only during a time duration of the fourth sequence.

10. The system according to claim 9, said second electronic module comprising electronic components for storing energy necessary to be supplied during the first, second and third sequence.

11. The system according to claim 1, said signals on said second electrical conductors being bidirectional.

12. The system according to claim 1, the communications of the second electronic module to the first electronic module through said second electrical conductors being in current loop by activation of different currents.

13. Method for surgical system comprising:
power supplying a rotary motor for driving a tool of a surgical instrument by a first electronic module of a control device of said instrument through first electrical conductors dedicated to the supply of said rotary motor;
power supplying and/or controlling said control device by said first electronic module of said control device through second electrical conductors distinct from the first electrical conductors,
said second electrical conductors carrying a number of signals greater than the number of said second electrical conductors.

14. The method according to claim 13, further comprising sending on said second electrical conductors of cycles of N periodic sequences, N being a positive number.

15. The method of claim 14, further comprising:
sending by said first electronic module a first sequence corresponding to a clock signal to the second electronic module;
sending by said first electronic module a second sequence corresponding to said second electronic module;
sending by said second electronic module a third sequence corresponding to said first electronic module;
sending by said first electronic module a fourth sequence corresponding to said supply signal and/or supply signal of an accessory and/or to the power supply signal of organs or auxiliary functions to said second electronic module.

* * * * *